(12) United States Patent
Heiss-Chouquet et al.

(10) Patent No.: US 10,416,055 B2
(45) Date of Patent: Sep. 17, 2019

(54) METHOD AND APPARATUS FOR DETERMINING THE EDGE STRENGTH OF PLATE-SHAPED ELEMENTS MADE OF BRITTLE-FRACTURE MATERIAL

(71) Applicant: SCHOTT AG, Mainz (DE)

(72) Inventors: Markus Heiss-Chouquet, Bischofsheim (DE); Kurt Nattermann, Ockenheim (DE); Clemens Ottermann, Hattersheim (DE)

(73) Assignee: SCHOTT AG, Mainz (DE)

( * ) Notice: Subject to any disclaimer, the term of this patent is extended or adjusted under 35 U.S.C. 154(b) by 282 days.

(21) Appl. No.: 15/444,656

(22) Filed: Feb. 28, 2017

(65) Prior Publication Data

US 2017/0167960 A1 Jun. 15, 2017

Related U.S. Application Data

(63) Continuation of application No. 14/814,540, filed on Jul. 31, 2015, now Pat. No. 9,664,603.

(30) Foreign Application Priority Data

Jul. 31, 2014 (DE) .................. 10 2014 110 856

(51) Int. Cl.
*G01N 3/10* (2006.01)
*G01N 33/38* (2006.01)
(Continued)

(52) U.S. Cl.
CPC ............... *G01N 3/10* (2013.01); *G01N 3/08* (2013.01); *G01N 3/20* (2013.01); *G01N 33/386* (2013.01);
(Continued)

(58) Field of Classification Search
CPC .. G01N 3/08; G01N 3/10; G01N 3/20; G01N 33/386; G01N 2203/0282; G01N 2203/0067
(Continued)

(56) References Cited

U.S. PATENT DOCUMENTS 3,350,917 A 11/1967 Winklhofer
3,377,847 A * 4/1968 Aske .................. G01N 3/10
60/534

(Continued)

FOREIGN PATENT DOCUMENTS

AT 411714 4/2004
DE 141571 5/1980
(Continued)

OTHER PUBLICATIONS

English translation of Nattermann et al.: "Bruchstatistik" [Fracture Statistics] in "Festigkeit von Glas—Grundlagen and Messverfahren" [Strength of Glass—Basics and Methods of Measurement], ISBN3-921089-30-1, 11 pages.

(Continued)

*Primary Examiner* — Jonathan M Dunlap
(74) *Attorney, Agent, or Firm* — Ohlandt, Greeley, Ruggiero & Parle, L.L.P.

(57) ABSTRACT

An improved measurement method and a corresponding measurement device are provided that measure the edge strength of plate-shaped elements made of brittle-fracture material. For this purpose, a long sample is drawn apart at the short edges, wherein the force transmission points lie next to the center of gravity of the base surface of the sample.

3 Claims, 6 Drawing Sheets

(51) Int. Cl.
*G01N 3/08* (2006.01)
*G01N 3/20* (2006.01)

(52) U.S. Cl.
CPC ............ *G01N 2203/0067* (2013.01); *G01N 2203/0282* (2013.01)

(58) Field of Classification Search
USPC .............. 73/826, 828, 830, 834, 835, 856
See application file for complete search history.

(56) References Cited

U.S. PATENT DOCUMENTS

| | | | |
|---|---|---|---|
| 3,572,102 | A | 3/1971 | Baratta |
| 3,983,745 | A | 10/1976 | Juusola |
| 4,003,246 | A | 1/1977 | Cain |
| 4,753,115 | A | 6/1988 | Moody |
| 4,823,609 | A | 4/1989 | Yost |
| 4,916,954 | A | 4/1990 | Buzzard |
| 5,054,324 | A | 10/1991 | Pohl |
| 5,431,062 | A | 7/1995 | Baratta |
| 5,437,192 | A | 8/1995 | Kawamoto et al. |
| 5,594,178 | A | 1/1997 | Takahashi et al. |
| 5,892,157 | A | 4/1999 | Syre |
| 8,365,610 | B2 | 2/2013 | Decraecker et al. |
| 8,825,423 | B1 | 9/2014 | Brovold |
| 2002/0032117 | A1 | 3/2002 | Peuchert et al. |
| 2003/0076487 | A1 | 4/2003 | Cannon et al. |
| 2008/0083288 | A1 | 4/2008 | Glaesemann |
| 2013/0207058 | A1 | 8/2013 | Wegener et al. |
| 2013/0298692 | A1 | 11/2013 | Seok |
| 2013/0319048 | A1 | 12/2013 | Hartmann |
| 2014/0069203 | A1 | 3/2014 | McColskey et al. |
| 2014/0083198 | A1 | 3/2014 | Sharps et al. |
| 2014/0352451 | A1 | 12/2014 | Kismarton |

FOREIGN PATENT DOCUMENTS

| | | |
|---|---|---|
| DE | 233187 | 2/1986 |
| DE | 69001746 | 9/1993 |
| DE | 19540891 | 5/1996 |
| DE | 19637808 | 12/1997 |
| DE | 102007005671 | 8/2008 |
| DE | 102012104594 | 12/2013 |
| JP | S58101420 | 6/1983 |
| JP | H0378641 | 4/1991 |
| JP | 2004184238 | 7/2004 |
| JP | 2010506168 | 2/2010 |
| JP | 2011033376 | 2/2011 |
| JP | 2011202991 | 10/2011 |
| JP | 2012247208 | 12/2012 |
| JP | 2014002018 | 1/2014 |

OTHER PUBLICATIONS

Yan et al., "SIFS of Rectangular Tensile Sheets with Symmetric Double Edge Defects", Journal of Mechanics of Materials and Structures, vol. 5, No. 5, 2010. Accessed online Nov. 14, 2016. pp. 795-803. <http://msp.org/omms/2010/5-5/jomms-v5-n5-p06-p.pdf>.

Zhang, "Design of Eccentric Tension Mechanism Used on Universal Material Testing Machine", Physics Examination and Testing, vol. 29, No. 3, May 2011, with English abstract, 3 pages.

* cited by examiner

METHOD AND APPARATUS FOR DETERMINING THE EDGE STRENGTH OF PLATE-SHAPED ELEMENTS MADE OF BRITTLE-FRACTURE MATERIAL

CROSS REFERENCE TO RELATED APPLICATIONS

This application is a continuation of U.S. application Ser. No. 14/814,540 filed Jul. 31, 2015, which claims benefit under 35 U.S.C. § 119(a) of German Patent Application No. DE 10 2014 110 856.6 filed Jul. 31, 2014, the entire contents of all of which are incorporated herein by reference.

BACKGROUND OF THE INVENTION

1. Field of the Invention

The invention relates generally to the determination of strength parameters of materials. In particular, the invention relates to the determination of the strength of brittle-fracture materials, such as glass, glass ceramics, or ceramics. The invention is used more preferably for the determination of the fracture strength of glass panes.

2. Description of Related Art

Brittle-fracture materials behave differently from ductile materials, for example, in regard to failure under a load. Ductile materials, in particular many metals, expand under a bending or tensile load up to the elastic limit and then break apart at a relatively well-defined load. The fracture of brittle-fracture materials, by contrast, does not occur at a strength limit in terms of a material characteristic value, but rather statistically with a probability that depends on the acting tensile stress. The parameters of the fracture probability distribution (for example, normal or Weibull distribution) depend primarily on the processing of the samples—but, in contrast to ductile materials, they depend only slightly on the material.

In order to acquire knowledge on the strength of brittle-fracture materials, it is necessary to carry out fracture tests. The parameters of a fracture strength distribution, among other things, can then be derived from these tests.

If a plate-shaped element made of brittle-fracture material is subjected to bending, an additional effect is that the strength is significantly determined by the fracture strength of the edges of the element. Fractures that thereby occur in a surface area are generally less common than fractures that originate from one of the edges of the element.

Methods are known, with which the edge strength of thin glass can be determined without any contact. The US 2014/0083198 A1 describes, for example, a method in which plates are heated along the edge locally and without any contact. This results in the creation of tensile stress at the plate edges. Measurements using this method are costly in terms of time, however, and are not suitable either for obtaining statistical strength data or for process monitoring. Moreover, they fundamentally fail in the case of glasses exhibiting low expansion (low thermal expansion coefficient), such as those utilized in electronic devices, for example.

SUMMARY

The invention is based then on the object of providing an improved measurement method and a corresponding measurement device, with which the edge strength of plate-shaped elements made of brittle-fracture material can be measured.

BRIEF DESCRIPTION OF THE DRAWINGS

The invention will be explained below on the basis of the appended figures. In the figures, identical reference numbers refer to identical or corresponding elements. Shown are.

DETAILED DESCRIPTION

A fundamental problem in evaluating the mechanical properties of glass articles is, first of all, the statistical nature of the strength of brittle materials. Glass has no strength in terms of an elastic limit, for instance, as in the case of ductile materials, but rather fracture statistics, which, for example, are characterized by a mean value and scatter. The measurement of glass strength, therefore, needs to be carried out on an adequate number of random samples (see, for example: K. Nattermann, A. Habeck: "Bruchstatistik" [Fracture Statistics] in "Festigkeit von Glas—Grundlagen and Messverfahren" [Strength of Glass—Basics and Methods of Measurement], ISBN3-921089-30-1). Particularly for production monitoring, so-called control charts are also useful (for example, in accordance with ISO 7870) for indicating tendency directions/deviations of target values.

Figure 1:
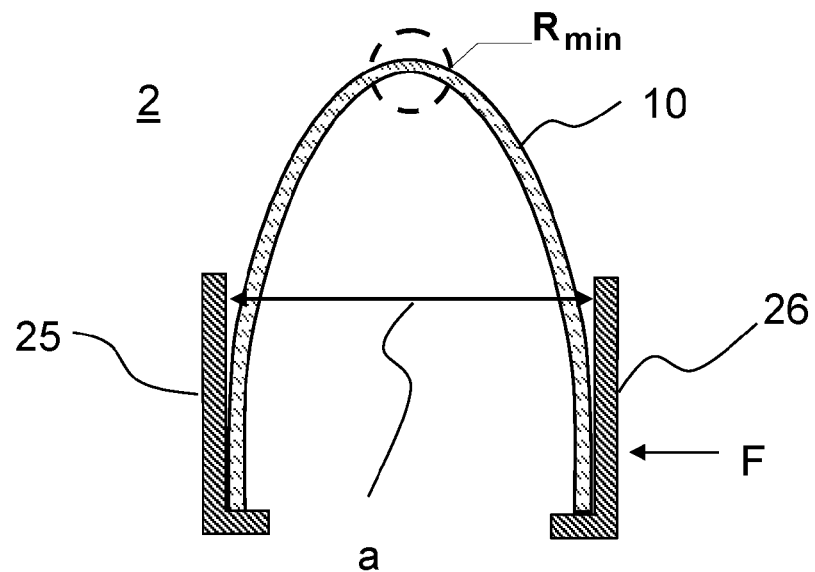
FIG. 1 a conventional measurement arrangement for measuring the fracture strength of plate-shaped, brittle-fracture elements, FIG. 2 a strip-shaped sample made of brittle-fracture material, which is provided at its ends with retainers of a measurement arrangement according to the invention, FIG. 3 the arrangement illustrated in FIG. 2 in plan view onto an edge of the sample, FIG. 4 a distribution of lines of identical mechanical stresses (isobars) in a strip-shaped sample, FIG. 5 a measurement arrangement for carrying out the method according to the invention, FIG. 6 a roll of a ribbon of glass having a bending radius determined according to the invention, FIG. 7 to FIG. 9 maximum and minimum bending radii for a bending test of a glass article as a function of statistical parameters obtained from fracture tests, and FIG. 10 a glass article in the form of a ribbon of glass, on which a local bend having a bending radius predetermined by rolling is imposed.

The edge strength of thin glasses can be determined by means of the 2-point bending method. FIG. 1 shows a measurement arrangement 2 for carrying out this method. In this method, thin glass samples 10 are clamped between two support plates 25, 26 and then bent by bringing together these plates 25, 26.

In this case, an inhomogeneous state of stress, which is greatest in the middle of the sample 10, is created over the sample. Accordingly, the bending radius of the sample 10 is the smallest also in the middle between the two support plates 25, 26.

The tensile stress at break can then be determined by determining the minimum bending radius $R_{min}$ that exists at break and by determining the corresponding tensile stress at the edge on the basis of this value. Here, the tensile stress ◻ is inversely proportional to the bending radius. The bending radius $R_{min}$, in turn, depends on the distance a between the two support plates 25, 26. In order to determine the tensile stress at break of the sample 10, the distance a between the two support plates 51, 52 can thus be recorded simply at the time point of fracture.

The length of the measurement region in this method is variable, however, and becomes smaller the greater the edge strength. In general, the measurement results on small samples are used in order to estimate the strength of markedly larger products. In doing so, the following relation can be used for calculating the probability of failure:

$$F_{product}=1-(1-F_{sample})^L$$

The exponent L is given by: $L=Length_{product}/Length_{sample}$

Here, $F_{sample}$ and $F_{product}$ are the probabilities of failure of the measurement sample and the end product, respectively; $L_{sample}$ is the measurement length on the measurement sample; and $L_{product}$ is the edge length of the end product.

As can be seen, the ratio between the edge length of product and sample is in the exponent of the formula, for which reason its influence on the result is very large. Correspondingly, the uncertainty in the calculated probability of failure of the product also increases with larger exponents.

In the 2-point bending method, owing to the very short measurement length due to the method, this ratio and thus also the uncertainty in the determination of the probability of failure is very great for large products. In addition, a "reduced sample length" is incorporated into the ratio $Length_{product}/Length_{sample}$ and has to be calculated individually for each sample. This is due to the fact that the bending stress is distributed inhomogeneously over the sample length and thus a "fictive" measurement length has to be calculated using constant stress. Additional assumptions are incorporated into this calculation and further increase the inaccuracy of the result for a large sample.

Because, in this method, the entire sample 10 is bent, both edges of the sample 10 are also always tested in terms of their strength. If, in a sample 10, the two edges are prepared by different methods, then this measurement method can be used only to test the preparation method that produces the poorer strength quality.

In the following, the invention will be described in exemplary embodiments on the basis of strip-shaped samples of thin glasses. However, the invention can also be applied in an identical way to other plate-shaped elements. Unless otherwise stated, instead of a thin glass or a thin glass sample, it is also possible to use another brittle-fracture material, in particular glass ceramics or ceramics.

In summary, the drawbacks of the measurement methods that are conventional at present are composed of the following points: The measurement length is very short. This leads to large uncertainties in the recalculation for large samples. The stress distributions over the sample length are inhomogeneous. This, too, leads to further uncertainties in the recalculation for large samples. Both edges are equally subjected to stress, so that differently prepared edges cannot be measured independently of each other. The bending of the entire sample also places the surface area under high tensile stress in the direction of the bending axis, as a result of which, depending on the quality of the edge and the surface, fractures can occur on the surface.

The method is suitable only for samples of homogeneous thickness, because, otherwise, the approximation methods that are used for calculation of the ensuing bending deformation are no longer valid.

The measurement method and the measurement arrangement according to the invention solve practically all five of the above-mentioned drawbacks of the hitherto conventional 2-point bending method: samples of practically any length can be used, the stresses in the samples are largely constant over the measurement range, the tensile stress is markedly different at the two sample edges, so that the fracture preferably originates from an edge that can be predetermined and can thus be investigated largely independently of the other edge, the tensile stresses on the surfaces are markedly reduced by the imposed stress profile, inhomogeneously thick samples, the thickness distributions of which are known, can also be investigated by this method, because an analytical solution exists for calculating the stress distribution.

The object is then achieved according to the invention in that a long sample is pulled apart at the short edges (tensile test). The points at which force is hereby transmitted preferably lie next to the center of gravity of the base surface of the sample. If the point at which force is transmitted were to lie at the center of gravity, a constant tensile stress would ensue over the entire sample width. The shift of the point at which the force is transmitted imparts an additional torque, which leads to a typically linear or at least approximately linear, declining stress curve, which, in any case, however, originates from the edge, over the sample width.

Through suitable choice of the point at which force is transmitted or of the position thereof along the short edge of the sample, it is possible to adjust the ratio between the stresses at the tested edge and the opposite-lying edge, as a result of which testing of a chosen edge is possible.

Accordingly, the invention provides a method for determining the edge strength of plate-shaped elements made of brittle-fracture materials, in which a strip-shaped sample made of brittle-fracture material is provided, which has two opposite-lying lateral faces and two lengthwise edges extending in the longitudinal direction of the sample. Each of the two ends of the strip-shaped sample is joined to a retainer. The two retainers are then pulled apart, so that the strip-shaped sample is subjected to a tensile stress directed in the longitudinal direction of the sample. The tensile force is hereby transmitted asymmetrically with respect to the center line of the sample running between the two lengthwise edges, so that a higher tensile force is exerted on one of the lengthwise edges than on the opposite-lying lengthwise edge. The tensile force is then increased until the sample breaks apart and the tensile force at break of the sample is recorded. Alternatively to this, the tensile force can also be increased only until a predetermined maximum value is reached. It can then be determined whether the sample withstands the maximum value of the tensile force. It is possible in this way to determine whether the plate-shaped material satisfies specific requirements placed on the edge strength.

If the sample is subjected to stress until it breaks apart in order to determine statistical parameters of the strength of the glass, the aforementioned method is repeated on a number of samples. Preferably, for determination of statistical strength parameters, such as, for instance, a Weibull distribution, at least 10 and preferably at least 20 samples are tested. For the embodiment with load up to the predetermined maximum value of tensile force, it is possible to repeat the method using a number of samples for determination of statistical values, such as, for instance, a probability of failure.

Figure 2:
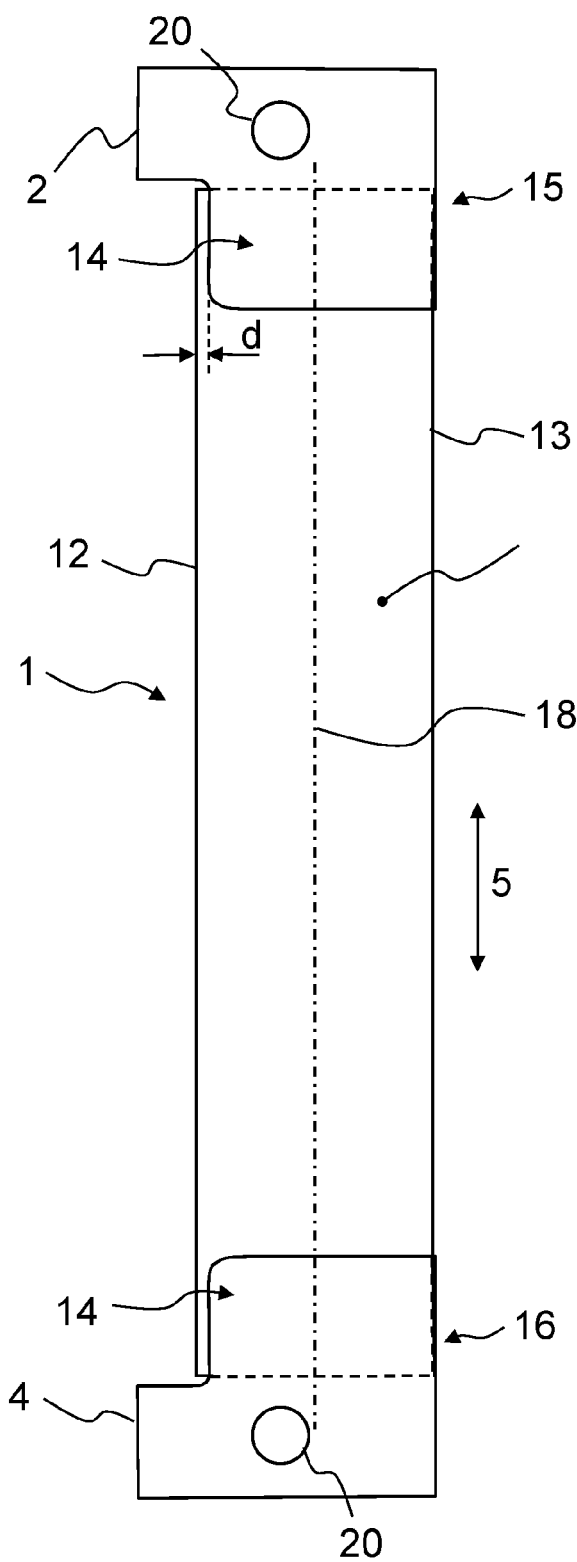
Figure 3:
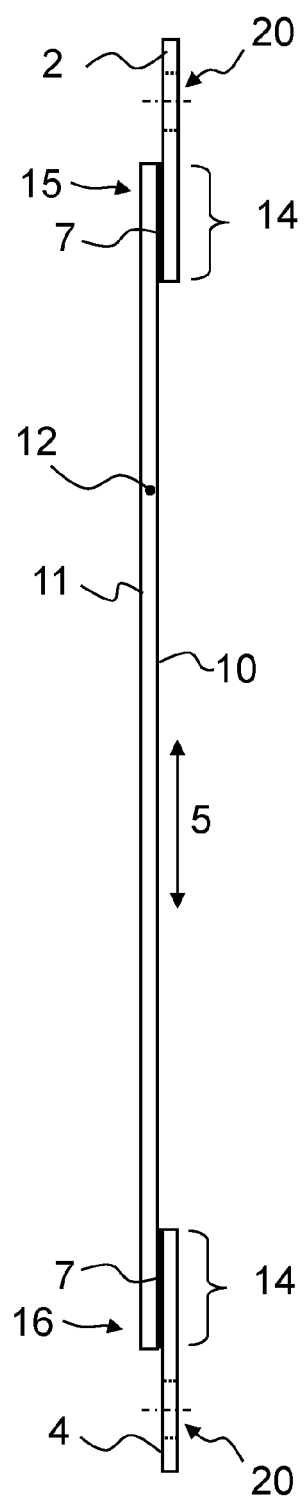

For explanation of the method, FIG. 2 shows a strip-shaped sample 1 in plan view on one of the lateral faces 10. FIG. 3 shows the arrangement in plan view on one of the lengthwise edges 12. Owing to the strip-shaped geometry of the sample 1, it has two lengthwise edges 12, 13 extending in the longitudinal direction 5. A respective retainer 2 or 4 is fastened at the ends 15, 16 of the strip-shaped sample 1.

The sample 1 can be of practically any length. However, it should preferably have a length of at least two times the base edge length in order to adjust a sufficiently homogeneous stress profile in the measurement range of the lengthwise edge. Accordingly, a sample is preferably used that has a length at least twice as long as its width. According to an exemplary embodiment, samples with the dimensions 20 mm×50 mm are used.

Without any limitation to the special form of the retainers 2, 4, as they are illustrated in the figures, metal is generally preferred as material for the retainers. Metal is capable of absorbing greater tensile forces in comparison to brittle-fracture materials, such as, in particular, glass. However, other materials that are stronger in terms of tensile stresses are also conceivable for the retainers. For example, plastic or a composite material can also be used for the retainers.

In order to test thin glasses having a thickness in the range of 20 μm to 300 μm, for example, preferably plate-shaped retainers 2, 4 having a thickness in the range of 0.1 mm to 0.5 mm are preferred. According to an exemplary embodiment, the retainers 2, 4 shown in FIGS. 2 and 3 have a thickness of 0.2 millimeter. Obviously, however, there is no limitation in terms of the glass thickness in regard to the applicability of the invention. Thus, thicker glasses, such as, for example, those with thicknesses up to 1.5 mm, can be tested by the method according to the invention, if need be with correspondingly thicker retainers 2, 4.

The method according to the invention can be applied, in particular, to thin glass samples, such as, for example, those with thicknesses t from the set {10 μm, 15 μm 20 μm, 25 μm, 30 μm, 35 μm, 40 μm, 45 μm, 50 μm, 55 μm, 65 μm, 70 μm, 75 μm, 85 μm, 100 μm, 110 μm, 120 μm, 145 μm, 160 μm, 180 μm, 200 μm, 210 μm, 250 μm}.

The retainers 2, 4 each have a force transmission device, which here is in the form of an eyelet 20 in order to transmit the applied tensile force onto the retainers 2, 4 via the fastening device and thus onto the strip-shaped sample 1. For example, the eyelets 20 can be suspended in suitable fastenings of a tensile device. The retainers 2, 4 are fastened to the sample 1 in such a way that the force transmission devices are offset with respect to the center line 18 of the strip-shaped sample 1 toward one of the edges 12, 13 of the sample 1. The force transmission devices define force transmission points, which represent the centers of gravity of the tensile force distribution. If eyelets 20 or pins complementary to them are used as force transmission devices, the force transmission point is located typically at the center of the eyelet or pin.

Preferably, the retainers 2, 4 are joined to the ends 14, 15 of the sample 1 by means of an adhesive connection 7. As adhesive connection 7, it is possible to use a one-component or two-component adhesive. According to yet another embodiment of the invention, a double-sided adhesive tape is also possible. The adhesive attachment is made within a fastening portion 14 of the retainer. In this case, the fastening portion 14 is the part of the retainer 2, 4 that overlaps the sample 1 and, in the example shown, defines the fastening surface area of the sample 1 with the respective retainer 2, 4.

As shown on the basis of FIG. 2 and FIG. 3, the connection of the sample 1 to the respective retainer 2, 4 is created over a surface area that has a width that is preferably as large as possible in the direction crosswise to the tensile direction. As a result, the distribution of the tensile stresses in the sample 1 is already as linear as possible as close to the retainer 2, 4 as possible. Owing to such a flat connection of the retainer 2, 4 to the sample 1, which extends over a large part of the sample width, excessive tensile stress at points in the sample 1 are also prevented insofar as possible.

Figure 4:
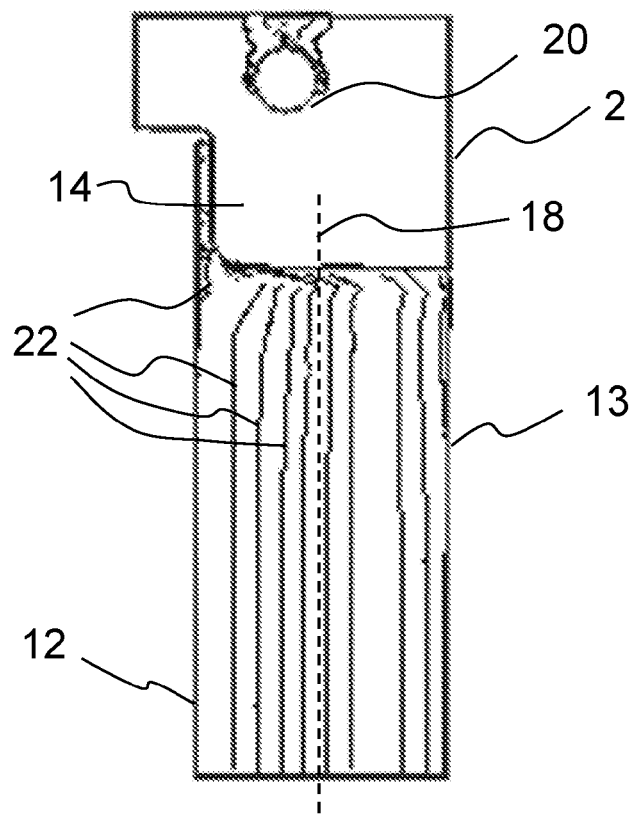

To highlight this, FIG. 4 shows a simulation of the stress distribution in the sample 1. Only one retainer and one lengthwise section of the sample 1 are illustrated. If, as preferred, similar retainers 2, 4 are used, then the stress profile is also symmetric with respect to the center of the sample 1. In the case illustrated in FIG. 4, the force transmission point or the position of the eyelet 20 is chosen in such a way that the stress at the lengthwise edge 13 is exactly zero.

The stress distribution is illustrated on the basis of tensile stress isobars 22, that is, lines of identical tensile stress in terms of amount. The eyelet 20, as force transmission device, is offset with respect to the center line 18 of the sample 1 in the illustration of FIG. 4 in the direction toward the lengthwise edge 12. Accordingly, a higher tensile stress is applied at the lengthwise edge 12 than at the opposite-lying lengthwise edge 13.

As can be seen on the basis of FIG. 4, the tensile stress isobars 22 are already parallel to the lengthwise edge 12 after a short lengthwise distance from the fastening portion 14 of the retainer 2. In this region, the tensile stress at the lengthwise edge 12 then also remains constant. In order to obtain such an unvarying tensile stress over the greatest possible length of the lengthwise edge to be tested, it is advantageous, as stated, when the fastening portion 14 extends over the greatest possible width of the strip-shaped sample. In general, without any limitation to the special design of the retainers 2, 4 shown in FIG. 2 to FIG. 4, it is therefore provided according to a preferred embodiment of the invention that at least one of the retainers 2, 4 is joined to the sample 1 in a flat manner, with the fastening surface area having a width that extends over at least ¾ the width, preferably over at least ⅚ the width, and more preferably over the [entire] width of the strip-shaped sample.

As can be seen on the basis of FIG. 3, in particular, it generally suffices to fasten, that is, to attach adhesively, the retainers 2, 4 only on one lateral face of the sample 1—here, on the lateral face 10. This facilitates the preparation of the samples 1. According to an embodiment of the invention, the retainers 2, 4 are therefore fastened on one side of one of the lateral faces 10, 11 of the sample 1. This leads intrinsically to differences in stress between the two lateral faces 10, 11. However, it has been found that these differences in stress are negligible. At higher forces, buckling of the sample can result. In this case, a second retainer can be fastened to the opposite-lying lateral face in a mirror-symmetric manner.

On the basis of the examples of FIG. 2 to FIG. 4, yet another advantageous enhancement of the invention can be seen. There is no overlap between the glass edge to be tested (in the example, the lengthwise edge 12) and the edge of the retainer 2, 4. Instead, the edge of the metal retainer runs over the short sample edge into the sample 1. The reason for this is that the simulations showed that, at the points at which the sample edge and the retainer edge cross, tensile stresses are created in the brittle-fracture material, such as, for example, in particular, in the glass, these stresses being clearly greater than the stresses in the measurement range. In other words, the retainer 2, 4 is thus fastened flatly on the sample 1 in such a way that the fastening surface area (given in the example by the surface area of the fastening portion 14) is distanced from the lengthwise edge 12 to be tested, that is, to the lengthwise edge on which the higher tensile force is exerted. In the examples shown, the fastening portion 14 is separated by a distance d from the lengthwise edge 12, which corresponds to roughly ⅛ of the width of the strip-shaped sample.

The greater the distance d is, however, the greater, too, is the distance from the fastening portion 14, at which the tensile stress isolines 22 become parallel at the lengthwise edge to be tested, so that the tensile stress remains constant along the lengthwise edge. In general, without any limitation to the exemplary embodiment, it is therefore provided in an enhancement of the invention that the distance of the fastening surface area from lengthwise edge is at most 1/10 of the width of the strip-shaped sample 1. On the other hand, in order to prevent the above-discussed effect of excessive tensile stress, it is generally preferred according to yet another enhancement of the invention that the distance of the fastening area from the lengthwise edge 12 is at least as large as the thickness of the sample 1. These aforementioned enhancements are suitable, in particular, for margins without borders. If, by contrast, owing to the manufacture of the glass pane, borders are present, then, according to another embodiment of the invention, the distance d should be at least as long as the border is wide. In other words, the fastening surface area in this case is preferably chosen in such a way that it lies next to the border in a region of essentially constant thickness. Borders are created by various methods of manufacture, such as, for instance, the down-draw method and the overflow fusion method as well as by drawing a ribbon of glass from a preform.

In the vicinity of the retainer 2, 4 for force transmission, the stresses are not homogeneous in the lengthwise edge to be measured. This can be seen in FIG. 4 on the basis of tensile stress isolines that do not run rectilinearly in the regions of the sample that are adjacent to the fastening portion 14. Only at a distance from the glass base edge of approximately twice the depth of the fastening surface area is an unvarying tensile stress applied to the lengthwise edge to be tested.

In this region around the retainers 2, 4 for force transmission, the edge stresses are markedly less than in the measurement region further remote from the base edge. If fractures should arise in this "retainer region," the samples should be discarded.

Via the approach in which balance of both forces and torques must prevail in the samples, it is possible to determine the stress at the lengthwise edges 12, 13 in a simple case with homogeneous thickness. The following relation applies to the balance of forces:

balance of forces: $F_z = \int_A \sigma dA$

The following relation further applies:

balance of torques: $(x_F - x_s) \cdot F_z = \int_A (x - x_S) \cdot \sigma dA$

Here, $F_z$ is the tensile or pulling force and $\sigma$ is the stress distribution in the sample 1. $x_s$ is the x coordinate of the center of gravity (the x axis runs along the width of the sample or perpendicular to the tensile direction) and is calculated here via:

center of gravity of the base area:

$$x_s = \frac{1}{A}\int_A x dA$$

If, in addition, it is taken into consideration that a linear stress curve prevails between the two lengthwise edges 12, 13 of the sample 1 (in the x direction, which refers to the direction perpendicular to the tensile or pulling direction or perpendicular to the edge of the sample), and the stress is homogeneous over the thickness of the sample (y direction), the following relation results of Equation (1):

linear stress curve: $\sigma = \sigma_{Edge1} - ((\sigma_{Edge1} - \sigma_{Edge2})/B) * X_z$ Thus, for each sample, the stress distribution in the sample can be calculated as a function of the force transmission point $x_F$. This also applies, in particular, for samples of inhomogeneous thickness when the thickness distribution is known. By using methods of technical mechanics, such as, for example, by means of a finite element calculation, it is also possible to calculate the distribution of the stresses and, in particular, to do so for any shapes and thickness distributions.

Furthermore, it is not necessary that a tensile stress exist over the entire width of the sample. Instead, it is possible that the tensile stress vanishes at one of the lengthwise edges or even that a compressive stress exists at the lengthwise edge that lies opposite to the lengthwise edge to be tested. However, the edge subject to the compressive force should be prevented from buckling. It is further valid that the tensile stress can be introduced so that at a lengthwise edge (in the example of FIG. 2, the lengthwise edge 12), the tensile stress is substantially greater than at the opposite-lying lengthwise edge (lengthwise edge 13 in FIG. 2). In this way, fractures originate predominantly from the edge subjected to greater stress.

Owing to the declining stress curve from one lengthwise edge to the other lengthwise edge according to Equation (1) and the example of FIG. 4, the area is subjected to markedly less stress than in the 2-point bending. Correspondingly, surface area fractures occur much more rarely.

Figure 5:
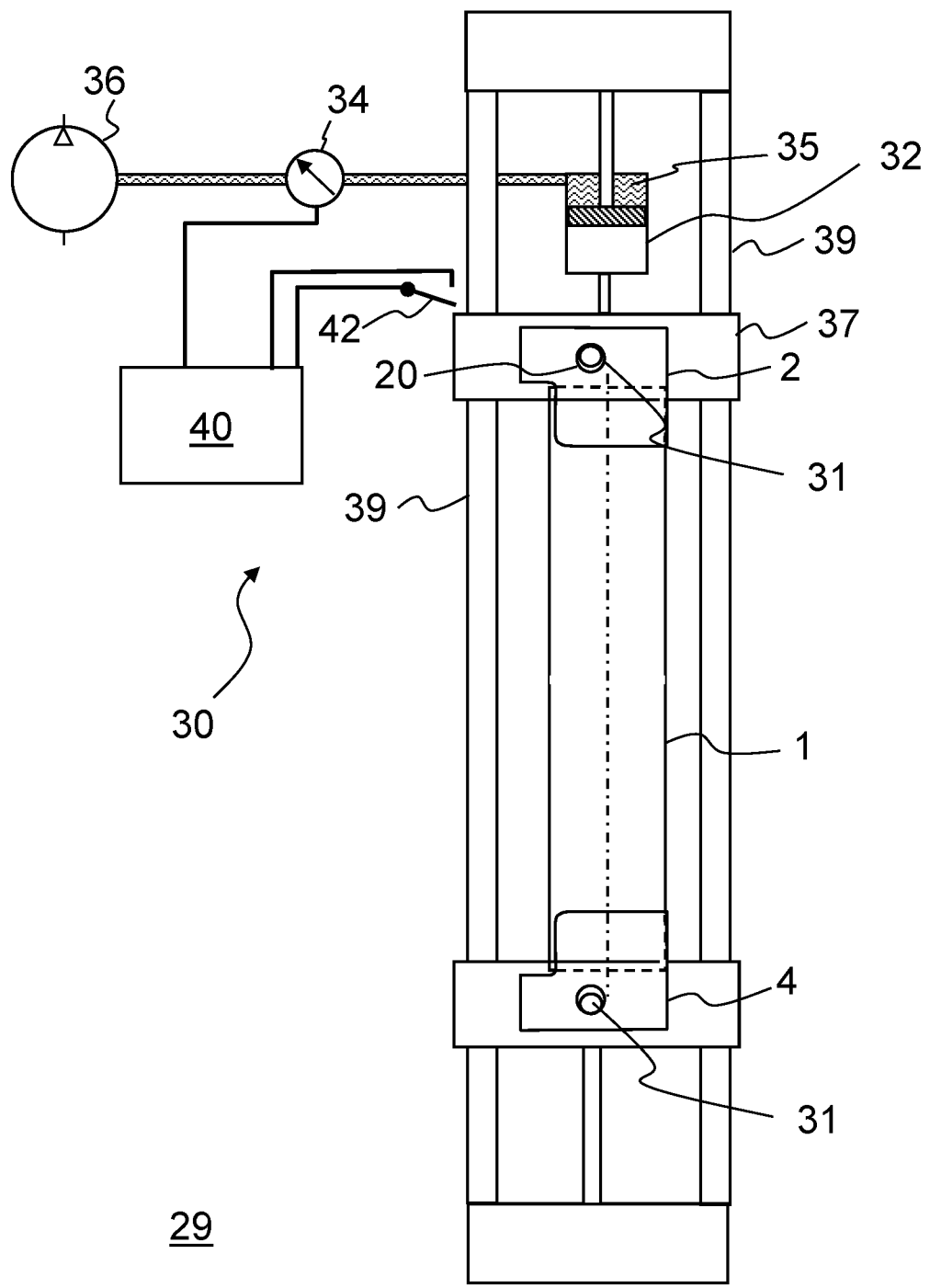

FIG. 5 shows an exemplary embodiment of an apparatus 29 for determining the edge strength of strip-shaped samples 1 made of brittle-fracture material.

The apparatus 29 according to the invention for determining the edge strength of plate-shaped, brittle-fracture materials generally comprises, without any limitation to the illustrated exemplary embodiment: two spaced retainers 2, 4 for fastening the ends of a strip-shaped sample 1 made of brittle-fracture material, as well as a tensile test device 30, which is set up so as to exert a tensile force on one of the retainers 2, 4, so that the tensile force is transmitted in the longitudinal direction of a strip-shaped sample 1 fastened to the retainers 2, 4, wherein the tensile test device 30 is further set up so as to increase the tensile force successively and to display or record the current value of the tensile force or of a value corresponding to the tensile force when the sample breaks apart under the exerted tensile force. Here, too, the tensile force can be increased up to a predetermined tensile force, with the tensile test device 30 being set up so as to record whether the sample withstands a predetermined maximum value of the tensile force or a value corresponding to the tensile force.

As already explained, the retainers 2, 4 have force transmission devices in order to transmit the tensile force of the tensile test device 30 to the retainers 2, 4, with these force transmission devices being arranged laterally offset to the middle of the fastening portions 13 of the retainers 2, 4 as viewed perpendicular to the tensile direction, so that the tensile force on the lengthwise edges 12, 13 of a sample 1 fastened to the retainers 2, 4 differs.

In order to prevent falsification of the measured values, it is advantageous when any torsion of the sample 1 is prevented during the test. For this purpose, according to an enhancement of the invention, two carriages 37 are used, as in the example shown in FIG. 5, both of which run on the same guide rails 39 and thus can move only along the axes with respect to each other.

Situated on each of these carriages 37 is a pin 31, in which the retainers 2, 4 together with their eyelets 20 can be hooked.

According to an enhancement of the invention, the tensile test device 30 comprises a pneumatic or hydraulic tensile device 32. For this purpose, in the illustrated example, one of the carriages 37 is joined to the frame of the mounting of the guide rails 39 via a pneumatic cylinder. If the tensile device 32 is supplied with an operating fluid 35 under pressure, then the pneumatic cylinder exerts a force on the carriage 37, so that the carriage is directed along the guide rails away from the opposite-lying retainer 37.

A hydraulic or pneumatic tensile device 32 is advantageous, because the tensile force exerted on the sample can easily be calculated on the basis of the pressure of the operating fluid 35. According to yet another enhancement of the invention, therefore, a pressure sensor 34 for recording the pressure of the operating fluid 35 of the pneumatic or hydraulic tensile device 32 is provided. The pressure of the operating fluid thus represents a value corresponding to the tensile force. Suitable as an operating fluid 35 is air, for example.

The pressure sensor 34 is connected to a recording device 40, which can record and/or display the pressure values. If the pressure of the operating fluid 35 is then successively increased by means of a pressure source 36 and the sample 1 breaks apart under the tensile force exerted by means of the pressurized operating fluid 35, the current value of the tensile force or of a value corresponding to the tensile force is displayed and/or recorded by the recording device 40.

The pressure source can also be controlled by the recording device 40 or by an overriding control device, so as to increase the pressure gradually. According to a simple embodiment, however, the pressure source 36 can also be set up so as to increase the pressure of the operating fluid 35 in a time-controlled manner.

There are various possibilities for determining the point in time at which the sample 1 breaks apart and for reading off or saving in memory the tensile force applied at this point in time. For example, the pressure curve can be recorded and, in the event of an abrupt drop in pressure because of the loss of the opposing force of the sample due to breaking, when an abrupt drop in pressure occurs, the value prevailing prior to the drop can be displayed and/or recorded. Another simple possibility consists in providing a switch 42, which is actuated by the carriage 37 that moves when the sample 1 breaks apart. The switch signal emitted by the switch 42 then triggers the recording of the current value of the tensile force or of a corresponding value, such as, for instance, the measured pressure value of the pressure sensor 34 in the example of FIG. 5.

A hydraulic or pneumatic production of the tensile or pulling force for testing of the sample 1 offers another special advantage. A number of pneumatic or hydraulic tensile devices 32 can be connected simultaneously to a pressure source 36. Accordingly, it is also possible to test a number of samples 1 simultaneously by using the tensile devices 32. The pressure of the operating fluid then results in application of an identical tensile force to the samples 1 when the tensile devices 32 are identical. The tensile force or the pressure of the operating fluid can then be successively increased until all samples 1 have broken apart. Each break is detected and the respectively current tensile force at break or the value corresponding to the tensile force is recorded.

According to an embodiment of the invention, therefore, a number of samples are pulled or drawn apart at their two retainers 2, 4 simultaneously, with the tensile force for drawing apart the samples being produced pneumatically or hydraulically by means of a common, pressurized operating fluid.

The invention is suited, among other things, to determine the parameters of a fracture probability distribution under a bending load and, on the basis of these parameters, to determine a bending radius that an article made of the tested brittle-fracture material is able to withstand with sufficiently high probability. In the process, it is also possible to determine a pre-specified lifetime under the bending load with a predetermined maximum failure rate. For this purpose, an application is the reeling of ribbons of thin glass. Such reeling dispenses with the requirement of cutting up the ribbon of glass directly after it has been produced. Instead, a long ribbon of glass can be stored in this way and/or transported, so as, at a later point in time, to process it further by unreeling it and cutting it to size. A problem is posed here by the fact that, owing to the long length of the ribbon of glass (typical lengths are, for example, 20 to 300 meters), the probability of fracture also increases. However, a single fracture generally results in the entire roll of glass being unusable.

According to an aspect of the invention, therefore, the invention relates to a plate-shaped glass article, wherein the edge strength is examined for samples of such a glass article by the method according to the invention, a minimum bending radius is determined on the basis of the edge strength, and another glass article, which preferably is similar to the glass article from which the samples were obtained, is bent, wherein the bending radius is not less than the determined minimum bending radius. Regarded as similar glass articles are those glass articles that are produced from the same glass of identical thickness and have similarly produced edges.

In particular, as stated, the glass article can be a ribbon of glass, with the ribbon of glass being reeled to form a roll after the production thereof, wherein the bending radius at the inner side of the roll of glass is not less than the minimum bending radius.

Figure 6:
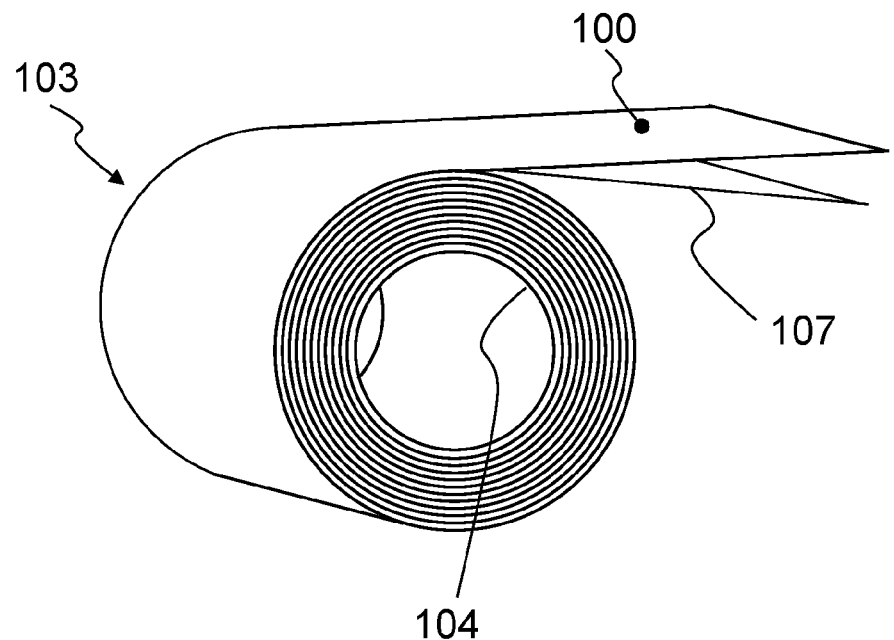

FIG. 6 shows such a roll of glass 103 composed of such a ribbon of glass 100. The inner side 104 of the roll of glass is formed by the innermost layer of the reeled ribbon of glass 100, with it also being possible to wind the ribbon of glass 100 on a core. As a result of the spiraled winding, the bending radius of the individual layers of the ribbon of glass 100 is larger toward the outside. Therefore, the minimum bending radius, which is a governing factor for the probability of fracture, exists at the inner side 104. In addition, in order to protect the glass material, a sheeting material 107 can be wound up with it, so that the individual layers of the ribbon of glass 100 do not lie directly on top of one another, but rather are separated by the sheeting material 107. As discussed further below, a glass article, such as, for example, a roll of glass 100, can be optimized by means of the invention in terms of a guaranteed strength and, at the same time, the most compact dimensions possible.

The glass article is preferably composed of a lithium aluminum silicate glass, a soda lime silicate glass, a borosilicate glass, an alkali aluminosilicate glass, or an alkali-free or low-alkali aluminosilicate glass. Such glasses are produced, for example, by means of drawing methods, such as a downdraw method, overflow fusion, or by means of float technology.

Advantageously, a low-iron or iron-free glass, in particular one with a $Fe_2O_3$ content of less than 0.05 wt %, preferably less than 0.03 wt %, can be used, because said glass has reduced absorption and thus makes possible, in particular, an increased transparency.

However, for other applications, gray glasses or colored glasses are also preferred.

According to an embodiment, a glass or a glass ceramic that is prestressed for its use is used. This glass or glass ceramic can be prestressed chemically by ion exchange or thermally or by a combination of thermal and chemical methods.

An optical glass can also serve as glass material, such as, for example, a dense flint glass, a lanthanum dense flint glass, a flint glass, a light flint glass, a crown glass, a borosilicate crown glass, a barium crown glass, a dense crown glass, or a fluorine crown glass Advantageously, a low-iron or iron-free glass, in particular one with a $Fe_2O_3$ content of less than 0.05 wt %, preferably less than 0.03 wt %, can be used, because said glass has reduced absorption and thus, in particular, an increased transparency.

For other applications, however, gray glasses or colored glasses are also preferred.

The invention is suited, in particular, for optimizing the mechanical properties of glasses that are already of high strength. High-strength glasses are typically used for applications in which the glasses are also subjected to a high mechanical load. Such glasses are consequently designed to withstand bending stresses acting on the surface area. In this case, in particular, the edges of the glasses represent significant weak points. Ultimately, a glass pane made of a high-strength glass indeed breaks quickly if the edge of the pane has flaws and is also subjected to a bending load. It is then possible to examine by means of the invention whether the edges remain constant in their quality when, for instance, individual glass panes are finished by dividing a larger pane. Thus, for example, it is conceivable that, owing to wear, a cutting wheel leaves behind damage at the glass edges. If this is the case, the strength of the entire glass pane is markedly diminished. The method can then be used to determine very precisely such changes in the manufactured product and to test the efficiency of improvements in the formation of edges. Given below are high-strength glasses for which an increase in strength can be achieved by monitoring the edge strength by means of the invention.

Suitable according to an embodiment are glasses having the following constituents, with the molar composition being given in mole percent:

| Constituent | mol % |
|---|---|
| $SiO_2$ | 56-70 |
| $Al_2O_3$ | 10.5-16 |
| $B_2O_3$ | 0-3 |
| $P_2O_5$ | 0-3 |
| $Na_2O$ | 10-15 |
| $K_2O$ | 0-2 |
| MgO | 0-3 |
| ZnO | 0-3 |
| $TiO_2$ | 0-2.1 |
| $SnO_2$ | 0-1 |
| F | 0.001-5 |

In addition, it applies as an auxiliary condition that the quotient of the molar content of fluorine to the molar content of $B_2O_3$, that is, $F/B_2O_3$, lies in a range from 0.0003 to 15, preferably from 0.0003 to 11, especially preferably 0.0003 to 10. These glasses can be prestressed chemically and can be used in mobile displays as cover glasses.

The composition in this case preferably contains the following components:

| Component | mol % |
|---|---|
| $SiO_2$ | 61-70 |
| $Al_2O_3$ | 11-14 |
| $B_2O_3$ | 0-0.5 |
| $Li_2O$ | 0-0.1 |
| $Na_2O$ | 11-15 |
| $K_2O$ | 0-2 |
| MgO | 0-3 |
| CaO | 0 (free) |
| ZnO | 0-1 |
| $CeO_2$ | 0-0.05 |
| $ZrO_2$ | 0 (free) |
| $SnO_2$ | 0-0.3 |
| F | 0.001-3 |
| $F/B_2O_3$ | 0.002-6 |

Especially preferably, the composition contains the following components:

| Component | mol-% |
|---|---|
| $SiO_2$ | 64-70 |
| $Al_2O_3$ | 11-14 |
| $B_2O_3$ | 0-0.5 |
| $Li_2O$ | 0-0.1 |
| $Na_2O$ | 11-15 |
| $K_2O$ | 0-2 |
| MgO | 0-3 |
| CaO | 0 (free) |
| ZnO | <0.1 |
| $CeO_2$ | 0-0.05 |
| $ZrO_2$ | 0 (free) |
| $SnO_2$ | 0-0.3 |
| F | 0.001-1 |
| $F/B_2O_3$ | 0.002-2 |

Preferred according to an enhancement of the invention are borosilicate glasses of the following glass compositions, composed of (in wt %):

| Component | |
|---|---|
| $SiO_2$ | 60-85 |
| $Al_2O_3$ | 1-10 |
| $B_2O_3$ | 5-20 |
| Total $Li_2O + Na_2O + K_2O$ | 2-16 |
| Total MgO + CaO + SrO + BaO + ZnO | 0-15 |
| Total $TiO_2 + ZrO_2$ | 0-5 |
| $P_2O_5$ | 0-2, | as well as, if need be, additives of coloring oxides, such as, for example, $Nd_2O_3$, $Fe_2O_3$, CoO, NiO, $V_2O_5$, $Nd_2O_3$, $MnO_2$, $TiO_2$, CuO, $CeO_2$, $Cr_2O_3$, rare earth oxides in contents of 0-5 wt % or, for "black glass," of 0-15 wt %, as well as refining agents, such as $As_2O_3$, $Sb_2O_3$, $SnO_2$, $SO_3$, Cl, F, $CeO_2$ of 0-2 wt %.

Alkali-free borosilicate glasses constitute another suitable group of glasses. In this case, the following compositions in weight percent are preferred:

| Component | wt % |
|---|---|
| $SiO_2$ | >58-65 |
| $Al_2O_3$ | >14-25 |
| $B_2O_3$ | >6-10.5 |
| MgO | 0-<3 |

-continued

| Component | wt % |
|---|---|
| CaO | 0-9 |
| BaO | >3-8 |
| ZnO | 0-<2 |

These glasses are also described in US 2002/0032117 A1, the content of which is also made the subject of the present application in full scope with respect to glass compositions and glass properties. A glass of this class is marketed by the applicant under the trade name AF32.

The following table lists the contents of components of further alkali-free borosilicate glasses as well as, in the right column, a composition range of a class of glasses having similar properties based on this glass:

| Component | Example wt % | Range (wt %) |
|---|---|---|
| $SiO_2$ | 70 | 67-73 |
| $Al_2O_3$ | 10 | 8-12 |
| $B_2O_3$ | 10 | 8-12 |
| CaO | 6 | 4-9 |
| BaO | 1 | 0.5-2 |
| SrO | 3 | 2-4 |

Yet another class of preferred glass types comprises borosilicate glasses having the following components in weight percent:

| Component | wt % |
|---|---|
| $SiO_2$ | 30-85 |
| $B_2O_3$ | 3-20 |
| $Al_2O_3$ | 0-15 |
| $Na_2O$ | 3-15 |
| $K_2O$ | 3-15 |
| ZnO | 0-12 |
| $TiO_2$ | 0.5-10 |
| CaO | 0-0.1 |

A glass of this class of glasses is the Schott glass D 263. Glasses with more precise compositions are also described in US 2013/207058 A1, the content of which is also made the subject of the present invention in full scope with respect to the compositions of the glasses and the properties thereof.

Soda lime glasses are also suitable. Listed in the following table are two exemplary embodiments and the proportion in weight percent of the components in accordance with a preferred composition range:

| | Glass 1 | Glass 2 | Range: |
|---|---|---|---|
| $SiO_2$ | 74.42 | 71.86 | 63-81 |
| $Al_2O_3$ | 0.75 | 0.08 | 0-2 |
| MgO | 0.30 | 5.64 | 0-6 |
| CaO | 11.27 | 9.23 | 7-14 |
| $Li_2O$ | 0.00 | 0.00 | 0-2 |
| $Na_2O$ | 12.9 | 13.13 | 9-15 |
| $K_2O$ | 0.19 | 0.02 | 0-1.5 |
| $Fe_2O_3$ | 0.01 | 0.04 | 0-0.6 |
| $Cr_2O_3$ | 0.00 | 0.00 | 0-0.2 |
| $MnO_2$ | 0.00 | 0.00 | 0-0.2 |
| $CO_3O_4$ | 0.00 | 0.00 | 0-0.1 |
| $TiO_2$ | 0.01 | 0.01 | 0-0.8 |
| $SO_3$ | 0.16 | 0.00 | 0-0.2 |
| Se | 0.00 | 0.00 | 0-0.1 |

The glass 2 is especially well suited for the manufacture of sheet glass by the float method.

According to an embodiment, further soda lime silicate glasses of the following compositions are used as glass, composed of (in wt %):

| Component | |
|---|---|
| $SiO_2$ | 40-80 |
| $Al_2O_3$ | 0-6 |
| $B_2O_3$ | 0-5 |
| Total $Li_2O + Na_2O + K_2O$ | 5-30 |
| Total $MgO + CaO + SrO + BaO + ZnO$ | 5-30 |
| Total $TiO_2 + ZrO_2$ | 0-7 |
| $P_2O_5$ | 0-2, | as well as, if need be, additives of coloring oxides, such as, for example, $Nd_2O_3$, $Fe_2O_3$, CoO, NiO, $V_2O_5$, $Nd_2O_3$, $MnO_2$, $TiO_2$, CuO, $CeO_2$, $Cr_2O_3$, rare earth oxides in contents of 0-5 wt % or, for "black glass," of 0-15 wt %, as well as refining agents, such as $As_2O_3$, $Sb_2O_3$, $SnO_2$, $SO_3$, Cl, F, $CeO_2$ of 0-2 wt %.

According to yet another embodiment of the invention, lithium aluminum silicate glasses of the following compositions are used for the glass material, composed of (in wt %):

| Component | |
|---|---|
| $SiO_2$ | 55-69 |
| $Al_2O_3$ | 19-25 |
| $Li_2O$ | 3-5 |
| Total $Na_2O + K_2O$ | 0-3 |
| Total $MgO + CaO + SrO + BaO$ | 0-5 |
| ZnO | 0-4 |
| $TiO_2$ | 0-5 |
| $ZrO_2$ | 0-3 |
| Total $TiO_2 + ZrO_2 + SnO_2$ | 2-6 |
| $P_2O_5$ | 0-8 |
| F | 0-1 |
| $B_2O_3$ | 0-2, | as well as, if need be, additives of coloring oxides, such as, for example, $Nd_2O_3$, $Fe_2O_3$, CoO, NiO, $V_2O_5$, $Nd_2O_3$, $MnO_2$, $TiO_2$, CuO, $CeO_2$, $Cr_2O_3$, rare earth oxides in contents of 0-1 wt %, as well as refining agents, such as $As_2O_3$, $Sb_2O_3$, $SnO_2$, $SO_3$, Cl, F, $CeO_2$ of 0-2 wt %.

Further preferred for use as carrier material are alkali aluminosilicate glasses of the following glass compositions, composed of (in wt %):

| Component | |
|---|---|
| $SiO_2$ | 40-75 |
| $Al_2O_3$ | 10-30 |
| $B_2O_3$ | 0-20 |
| Total $Li_2O + Na_2O + K_2O$ | 4-30 |
| Total $MgO + CaO + SrO + BaO + ZnO$ | 0-15 |
| Total $TiO_2 + ZrO_2$ | 0-15 |
| $P_2O_5$ | 0-10, | as well as, if need be, additives of coloring oxides, such as, for example, $Nd_2O_3$, $Fe_2O_3$, CoO, NiO, $V_2O_5$, $Nd_2O_3$, $MnO_2$, $TiO_2$, CuO, $CeO_2$, $Cr_2O_3$, rare earth oxides in contents of 0-5 wt % or, for "black glass," of 0-15 wt %, as well as refining agents, such as $As_2O_3$, $Sb_2O_3$, $SnO_2$, $SO_3$, Cl, F, $CeO_2$ of 0-2 wt %.

Further preferably used as carrier material are alkali-free aluminosilicate glasses of the following glass composition, composed of (in wt %):

| Component | |
|---|---|
| $SiO_2$ | 50-75 |
| $Al_2O_3$ | 7-25 |
| $B_2O_3$ | 0-20 |
| Total $Li_2O$ + $Na_2O$ + $K_2O$ | 0-0.1 |
| Total MgO + CaO + SrO + BaO + ZnO | 5-25 |
| Total $TiO_2$ + $ZrO_2$ | 0-10 |
| $P_2O_5$ | 0-5, | as well as, if need be, additives of coloring oxides, such as, for example, $Nd_2O_3$, $Fe_2O_3$, CoO, NiO, $V_2O_5$, $Nd_2O_3$, $MnO_2$, $TiO_2$, CuO, $CeO_2$, $Cr_2O_3$, rare earth oxides in contents of 0-5 wt % or, for "black glass," of 0-15 wt %, as well as refining agents, such as $As_2O_3$, $Sb_2O_3$, $SnO_2$, $SO_3$, Cl, F, $CeO_2$ of 0-2 wt %.

Further preferably used are low-alkali aluminosilicate glasses of the following glass compositions, composed of (in wt %):

| Component | |
|---|---|
| $SiO_2$ | 50-75 |
| $Al_2O_3$ | 7-25 |
| $B_2O_3$ 0-20 | 0-20 |
| Total $Li_2O$ + $Na_2O$ + $K_2O$ | 0-4 |
| Total MgO + CaO + SrO + BaO + ZnO | 5-25 |
| Total $TiO_2$ + $ZrO_2$ | 0-10 |
| $P_2O_5$ | 0-5, | as well as, if need be, additives of coloring oxides, such as, for example, $Nd_2O_3$, $Fe_2O_3$, CoO, NiO, $V_2O_5$, $Nd_2O_3$, $MnO_2$, $TiO_2$, CuO, $CeO_2$, $Cr_2O_3$, rare earth oxides in contents of 0-5 wt % or, for "black glass," of 0-15 wt %, as well as refining agents, such as $As_2O_3$, $Sb_2O_3$, $SnO_2$, $SO_3$, Cl, F, $CeO_2$ of 0-2 wt %.

It is possible to use, for example, thin glasses, such as those of Schott AG, Mainz, marketed under the trade names D263, D263 eco, B270, B270 eco, Borofloat, Xensation Cover, Xensation cover 3D, AF45, AF37, AF 32, or AF32 eco.

In another embodiment, the brittle-fracture material is a glass ceramic, in particular in the form of a glass ceramic pane, wherein the glass ceramic is composed of a ceramized aluminosilicate glass or a lithium aluminosilicate glass, in particular of a chemically and/or thermally hardened, ceramized aluminosilicate glass or lithium aluminosilicate glass. In another embodiment, the brittle-fracture material comprises a ceramizable starting glass, which, in the event of a fire, is ceramized or continues to be ceramized under the action of heat and thereby brings about an increased fire protection safety.

Preferably, a glass ceramic or a ceramizable glass having the following composition of the starting glass is used (in wt %):

| Component | |
|---|---|
| $Li_2O$ | 3.2-5.0 |
| $Na_2O$ | 0-1.5 |
| $K_2O$ | 0-1.5 |
| Total $Na_2O$ + $K_2O$ | 0.2-2.0 |
| MgO | 0.1-2.2 |
| CaO | 0-1.5 |
| SrO | 0-1.5 |
| BaO | 0-2.5 |
| ZnO | 0-1.5 |
| $Al_2O_3$ | 19-25 |
| $SiO_2$ | 55-69 |
| $TiO_2$ | 1.0-5.0 |
| $ZrO_2$ | 1.0-2.5 |
| $SnO_2$ | 0-1.0 |
| Total $TiO_2$ + $ZrO_2$ + $SnO_2$ | 2.5-5.0 |
| $P_2O_5$ | 0-3.0 |

In another embodiment, a glass ceramic or a ceramizable glass having the following composition is preferably used as the starting glass (in wt %):

| Component | |
|---|---|
| $Li_2O$ | 3-5 |
| $Na_2O$ | 0-1.5 |
| $K_2O$ | 0-1.5 |
| Total $Na_2O$ + $K_2O$ | 0.2-2 |
| MgO | 0.1-2.5 |
| CaO | 0-2 |
| SrO | 0-2 |
| BaO | 0-3 |
| ZnO | 0-1.5 |
| $Al_2O_3$ | 15-25 |
| $SiO_2$ | 50-75 |
| $TiO_2$ | 1-5 |
| $ZrO_2$ | 1-2.5 |
| $SnO_2$ | 0-1.0 |
| Total $TiO_2$ + $ZrO_2$ + $SnO_2$ | 2.5-5 |
| $P_2O_5$ | 0-3.0 |

In another embodiment, a glass ceramic or a ceramizable glass having the following composition is preferably used as the starting glass (in wt %):

| Component | |
|---|---|
| $Li_2O$ | 3-4.5 |
| $Na_2O$ | 0-1.5 |
| $K_2O$ | 0-1.5 |
| Total $Na_2O$ + $K_2O$ | 0.2-2 |
| MgO | 0-2 |
| CaO | 0-1.5 |
| SrO | 0-1.5 |
| BaO | 0-2.5 |
| ZnO | 0-2.5 |
| $B_2O_3$ | 0-1 |
| $Al_2O_3$ | 19-25 |
| $SiO_2$ | 55-69 |
| $TiO_2$ | 1.4-2.7 |
| $ZrO_2$ | 1.3-2.5 |
| $SnO_2$ | 0-0.4 |
| Total $TiO_2$ + $SnO_2$ | Less than 2.7 |
| $P_2O_5$ | 0-3 |
| Total $ZrO_2$ + 0.87 ($TiO_2$ + $SnO_2$) | 3.6-4.3 |

The glass ceramic preferably contains high-quartz mixed crystals or keatite mixed crystals as predominant crystal phase. The crystallite size is preferably smaller than 70 nm, more preferably smaller than or equal to 50 nm, most preferably smaller than is equal to 10 nm.

The method or the apparatus according to the invention are then also suited to specify a fracture test for glass articles with large surface area, such as, for example, thin ribbons of glass 100, in particular in the form of a roll of glass 103 having a reeled ribbon of thin glass 100 in such a way that the glass article withstands a defined tensile load, in particular due to a bending load, guaranteed without breaking. For this purpose, the glass article can be subjected to a defined bending load prior to its further use or further processing, said defined bending load being indicated by using the data acquired by the method according to the invention. Accordingly, the glass article then withstands, in any case, a bending load of this magnitude with very high probability without any fracture. This embodiment of the invention will be explained below in more detail.

In the method according to the invention for determining the edge strength of plate-shaped, brittle-fracture materials, a random sample composed of N values for the fracture stresses $\sigma_1 \ldots \sigma_N$ is taken and the values of Equation 2:

$$R_i = \frac{E}{2\sigma_i} \cdot t_i$$

are calculated from these, with E referring to the modulus of elasticity of the glass and $t_i$ referring to the thickness of the i-th sample at the edge. The values $R_i$ are bending radii corresponding to the tensile stresses at which the edges would be stressed with identical tensile stress. From these values, in turn, a mean value <R> for the bending radius and a variance s are calculated for the random samples, preferably according to Equations 3 and 4, respectively:

$$\langle R \rangle = \frac{1}{N} \sum_{i=1}^{N} R_i, \text{ and}$$

$$s = \sqrt{\frac{1}{N-1} \sum_{i=1}^{N} (R_i - \langle R \rangle)^2}.$$

Figure 7:
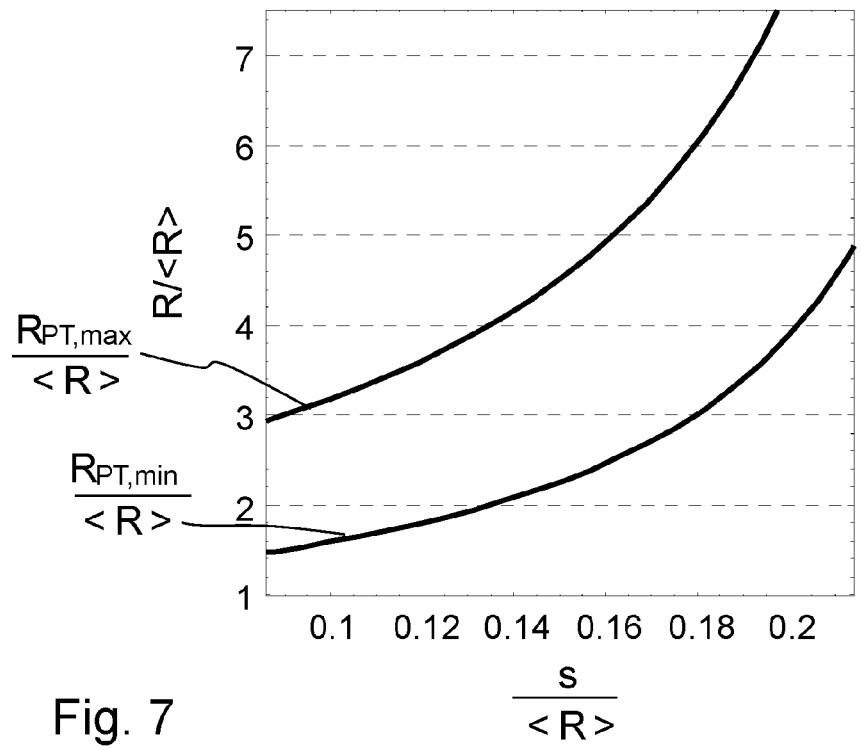

The entire glass article, in particular a glass sheet, is then bent, so that, depending on the relative variance s/<R>, its bending radius $R_{PT}$ for the two bending directions lies in the region defined by the curves in FIG. 7, that is, between the two curves $R_{PT,max}$ and $R_{PT,min}$. The bending can be produced by passing the glass article over rollers. In the diagram shown in FIG. 7, the ratio of the bending radius of the glass article to the mean value <R> of the bending radius when the samples 1 break is plotted on the ordinate as a function of the relative variance s/<R>.

It is preferred that the number of random samples N is at least 20, that 10% of the largest values and 10% of the smallest values for the tensile stress or the corresponding bending radii $R_i$ are discarded from the random sample, and that, from the rest (the so-called "supported random samples"), only the mean value and the variance are derived according to Equations (3) and (4). The glass article can then be bent, preferably by drawing it over rollers, so that, depending on the relative variance s/<R>, the bending radius $R_{PT}$ thereof lies in the region defined by the curves $R_{PT,min}$ and $R_{PT,max}$ in FIG. 8 for the two opposite bending directions.

The values $R_{PT,max}$ and $R_{PT,min}$ are functions of the relative variance s/<R>. If the relative variance is high, this means that there is a large scatter of the bending stresses or, correspondingly, the bending radii in the fracture tests. Correspondingly, with higher scatter, larger bending radii are also chosen for the fracture test of the entire glass article in order to be able to ensure a given fracture strength corresponding to the chosen bending radius.

Figure 8:
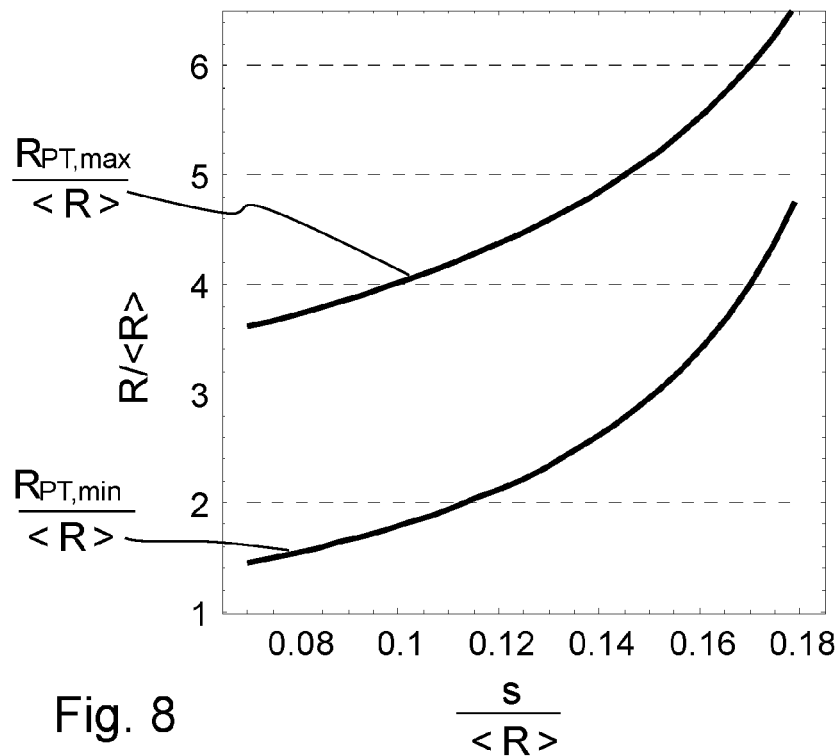

By choosing a bending radius between the curves $R_{PT,max}$<R>(s/<R>) and $R_{PT,min}$/<R> (s/<R>) according to FIG. 7 or FIG. 8, which are oriented to the relative variance of the fracture strength of samples of an equivalent glass article and define a narrow range with a bending radius that is as small as possible, it is possible to ensure very high fracture strength and still limit the rejects in the fracture test to glass articles that actually have significant weak points.

Figure 9:
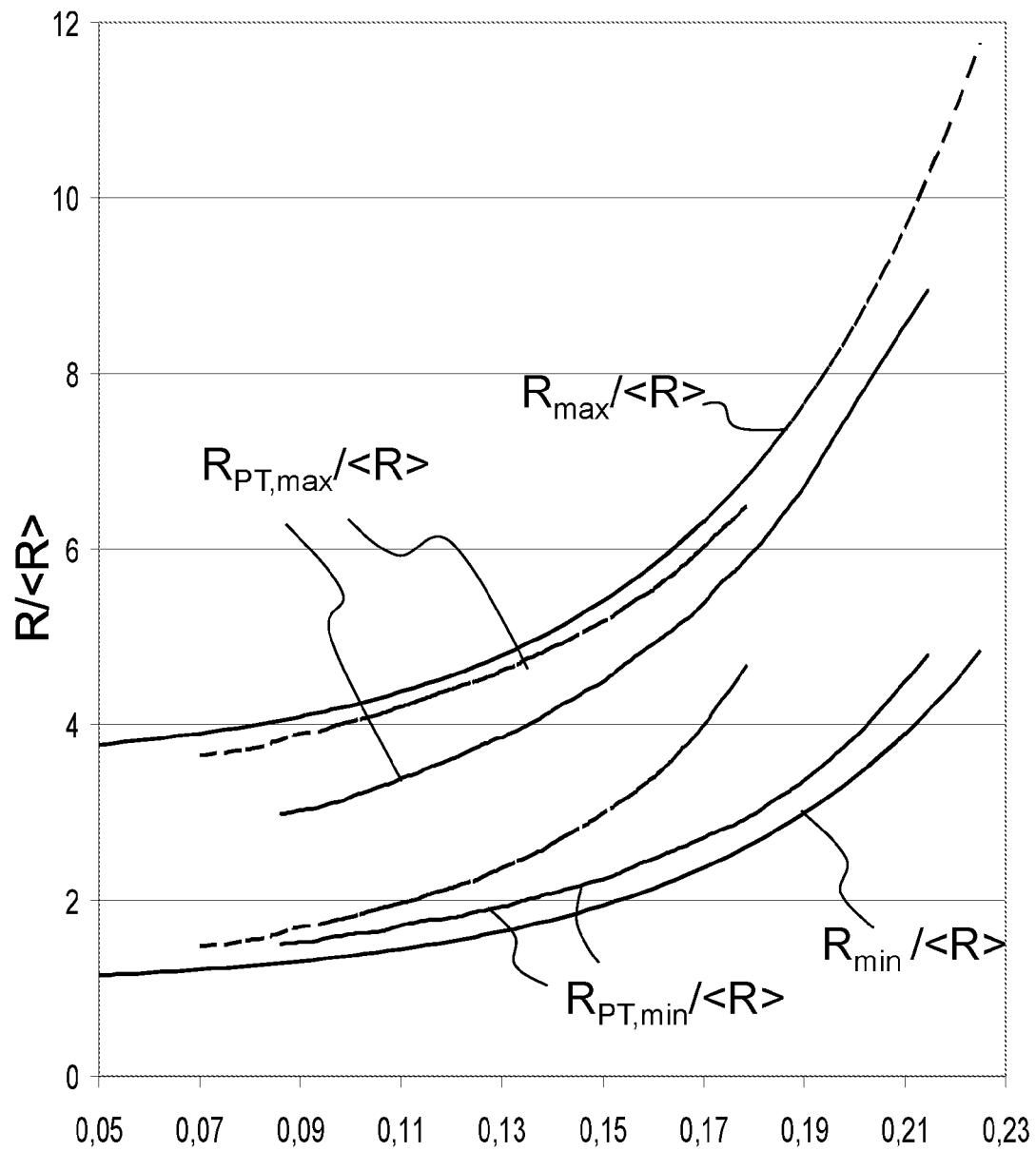

The regions between the curves $R_{PT,max}$/<R> and $R_{PT,min}$/<R> of FIG. 7 and FIG. 8 are slightly displaced against each other. For both of the test conditions mentioned above, namely, on the one hand, that of a random sample for which the values in the range of $R_{PT,max}$/<R> to $R_{PT,min}$/<R> according to FIG. 7 are favorable and, on the other hand, that of an adjusted random sample for which corresponding bending radii in the range of $R_{PT,max}$/<R> to $R_{PT,min}$/<R> result according to FIG. 8, it is possible to specify an enveloping range. For this purpose, FIG. 9 shows the curves $R_{PT,max}$/<R> and $R_{PT,min}$/<R> of FIGS. 7 and 8 as well as preferred limit values $R_{min}$/<R> (s/<R>), $R_{max}$<R> (s/<R>), between which the curves $R_{PT,max}$/<R> and $R_{PT,min}$/<R> lie. According to an embodiment of the invention, the bending radius for the fracture test of the entire thin, flat glass article is therefore chosen in such a way that it lies in the range of $R_{min}$(s/<R>), $R_{max}$(s/<R>). In this case, the following relations can be employed for the bending radii $R_{min}$(s/<R>), $R_{max}$(s/<R>):

$$\frac{R_{min}}{\langle R \rangle} = 1 + \exp\left(\frac{s}{\langle R \rangle \cdot 0.053} - 2.9\right), \text{ and}$$

$$\frac{R_{max}}{\langle R \rangle} = 3.5 + \exp\left(\frac{s}{\langle R \rangle \cdot 0.051} - 2.3\right).$$

Accordingly, the invention also relates to a method for providing a plate-shaped glass article having high fracture strength (for example, a ribbon of thin glass 100 or a roll of glass 103), in which: by means of a method according to the invention for determining the edge strength of plate-shaped, brittle-fracture material, a number of samples 1 (total number N) are used to evaluate the tensile stress at which each of the samples 1 breaks, from these values, the mean value <R> of the bending radii $R_i$, which corresponds to the tensile stress at which each of the samples 1 has broken is calculated and, using the mean value <R>, the variance s is preferably calculated according to:

$$s = \sqrt{\frac{1}{N-1} \sum_{i=1}^{N} (R_i - \langle R \rangle)^2}$$

and wherein then a glass article made of the same glass material as the samples (1), preferably a ribbon of glass (100), is bent in order to test whether the glass article withstands a bending radius $R_{PT}$ or a corresponding tensile stress, wherein the bending radius $R_{PT}$ is chosen in such a way that it lies in the range of the radii $R_{min}$ to $R_{max}$, which are dependent on the relative variance s/<R> wherein the radii $R_{min}$ and $R_{max}$ are given by the above Equations i) and ii).

The radii $R_i$ can be determined, in particular, according to Equation (2).

A similar glass material in terms of the invention is understood to be a glass of the same composition and same thickness with similar edge processing. In particular, for this purpose, the samples 1 are themselves cut from the glass article. Alternatively, the samples 1 can be obtained from another glass article produced beforehand or afterward in the same way as the actual glass article to be provided. If, for example, the edges of the samples 1 tested by the method according to the invention differ from the edge or the edges of the glass article in terms of their characteristics, then it is no longer possible without anything further to draw conclusions on the edge strength of the glass article from the measurement results for the tensile strength of the samples 1.

Figure 10:
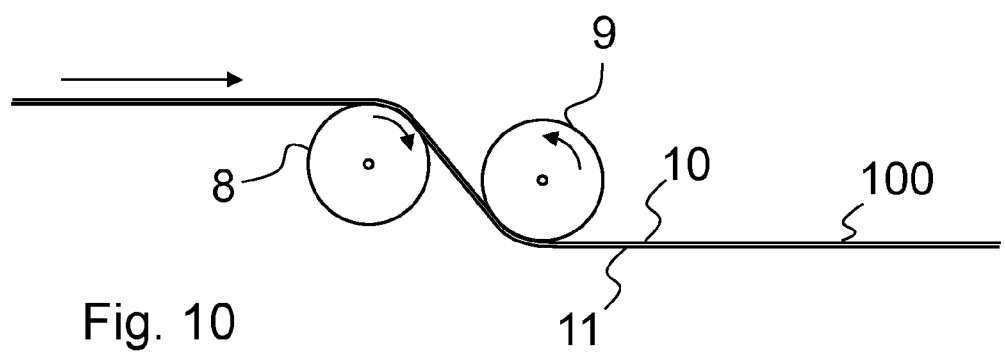

For this purpose, FIG. 10 shows schematically a glass article in the form of a ribbon of glass 100, which is advanced along the arrow and is guided over the rolls or rollers 8, 9, so that a bend having a bending radius $R_{PT}$ predetermined by the rollers 8, 9 is imposed locally on the ribbon of glass. The glass article is preferably tested with bends in opposite bending directions. For this purpose, in the example of FIG. 10, the rollers 8, 9 are arranged above and below the ribbon of glass 100, so that the ribbon of glass is bent with each of the two lateral faces 11, 12 around one of the rollers 8, 9.

According to an enhancement, in order to ensure that the entire glass article, which preferably has a very large surface area and is elongated, in the form of a ribbon of glass, withstands the bending stress with a bending radius in the range of $R_{min}$ to $R_{max}$, its longitudinal edges are bent along at least % of its total length, preferably along its entire length, at least with the bending radius $R_{PT}$.

As already mentioned, an adjusted random sample can be used for determining the values <R> (mean value of the bending radius at fracture) and s (variance of the bending radii at fracture), by determining the bending radii or tensile stresses at fracture for at least twenty samples, and a recalculation using Equation (2) is carried out, and the largest and smallest values, preferably 10% of the largest and smallest values, of the bending radius or tensile stress are discarded and the mean value and the variance are calculated by using the remaining values.

The embodiment of the invention described above can be then be used to produce a plate-shaped glass article having a guaranteed or predetermined fracture strength under a bending load at a predetermined bending radius, wherein the edge thereof or at least one edge of the glass article withstands a bending load with a bending radius $R_{PT}$ along its entire edge length, wherein the bending radius, corresponding to Equations i), ii) given above, lies in the range of $$R_{min} = \langle R \rangle \cdot \left\{ 1 + \exp\left( \frac{s}{\langle R \rangle \cdot 0.053} - 2.9 \right) \right\} \text{ to} \quad \text{i)}$$

$$R_{max} = \langle R \rangle \cdot \left\{ 3.5 + \exp\left( \frac{s}{\langle R \rangle \cdot 0.051} - 2.3 \right) \right\} \quad \text{ii)}$$

where <R> is the mean value and $$s = \sqrt{\frac{1}{N-1} \sum_{i=1}^{N} (R_i - \langle R \rangle)^2}$$

is the variance of the bending radii at fracture of a plurality von N samples made of the same glass material as the glass material of the glass article, with the bending radii $R_i$ at which each of the samples 1 breaks being determined preferably by means of the method according to the invention for examining the fracture strength of flat samples 1 made of brittle-fracture material.

It is especially preferred that the glass article is a thin ribbon of glass having a length of at least 20 meters, preferably at least 50 meters. Preferably, the ribbon of glass 100 is tested along the entire edge length of at least 20 meters for fracture strength and it is possible to ensure a corresponding bending radius that the ribbon of glass withstands.

It is obvious to the person skilled in the art that the invention is not limited to the exemplary embodiments described above, but rather can be varied in diverse ways, it being possible, in particular, to combine the features of the individual exemplary embodiments with one another.

LIST OF REFERENCE NUMBERS 1 sample
2, 4 retainers
5 longitudinal direction of 1
7 adhesive connection
10, 11 lateral face of 1
12, 13 lengthwise edge of 1
14 fastening portion of 2, 4
15, 16 ends
18 center line
20 eyelet
22 tensile stress isoline
25, 26 support plate
29 apparatus for determining the edge strength
30 tensile test device
31 pin
32 pneumatic or hydraulic pulling or tensile device
34 pressure sensor
35 operating fluid
36 pressure source
37 carriage
39 guide rail
40 recording device
42 switch
100 ribbon of glass
103 roll of glass
104 inner side 104 of 103
107 sheeting material

What is claimed is:

1. An apparatus for determining edge strength of a strip-shaped sample of brittle-fracture materials, comprising:
   two spaced retainers being configured for fastening two short ends of the strip-shaped sample when the strip-shaped sample has a length that is at least twice as large as a width at the two short ends; and
   a tensile test device configured to exert a tensile force on one of the retainers so that the tensile force is transmitted in a longitudinal direction of the strip-shaped sample, the tensile test device being further configured to increase the tensile force successively and to display or record the current value of the tensile force or of a value corresponding to the tensile force when the strip-shaped sample breaks apart under the exerted tensile force,
   wherein the retainers include force transmission devices that transmit the tensile force of the tensile test device onto the retainers, the force transmission devices being arranged laterally offset with respect to a center of a fastening portion of the retainers as viewed perpendicular to a pulling direction, so that the tensile force on the lengthwise edges of the strip-shaped sample differs.

2. The apparatus according to claim 1, wherein the tensile test device comprises a pneumatic or hydraulic tensile device.

3. The apparatus according to claim 1, further comprising a pressure sensor for recording a pressure of an operating fluid of the pneumatic or hydraulic tensile device.

* * * * *